(12) United States Patent
Strasly et al.

(10) Patent No.: US 8,822,219 B2
(45) Date of Patent: Sep. 2, 2014

(54) METHOD FOR PREPARING BIOLOGICAL TISSUES FOR USE IN BIOLOGICAL PROSTHESES

(75) Inventors: Marina Strasly, Baldissero Torinese (IT); Giovanni Rolando, Chivasso-Torino (IT)

(73) Assignee: Sorin Group Italia S.r.l., Milan (IT)

( * ) Notice: Subject to any disclaimer, the term of this patent is extended or adjusted under 35 U.S.C. 154(b) by 245 days.

(21) Appl. No.: 13/154,851

(22) Filed: Jun. 7, 2011

(65) Prior Publication Data

US 2011/0306123 A1 Dec. 15, 2011

(30) Foreign Application Priority Data

Jun. 9, 2010 (IT) .............................. TO2010A0487
May 26, 2011 (EP) .................................... 11167695

(51) Int. Cl.
- C12N 5/00 (2006.01)
- C12N 5/02 (2006.01)
- A61K 9/00 (2006.01)
- A61F 2/02 (2006.01)
- A61L 27/36 (2006.01)

(52) U.S. Cl.
CPC ................................. A61L 27/3683 (2013.01)
USPC .......... 435/422; 435/325; 424/400; 424/93.7; 623/23.72; 623/23.76

(58) Field of Classification Search
CPC ............ A61L 27/3683; A61L 27/3691; A61L 27/3839; C12N 5/0068; C12N 2533/90
USPC ........................ 435/422, 325; 424/400, 93.7; 623/23.72, 23.76
See application file for complete search history.

(56) References Cited

U.S. PATENT DOCUMENTS

| 4,755,593 | A | 7/1988 | Lauren |
| 5,873,812 | A | 2/1999 | Ciana et al. |
| 6,479,079 | B1 | 11/2002 | Pathak et al. |
| 2006/0110370 | A1 | 5/2006 | Pathak et al. |
| 2006/0193885 | A1 | 8/2006 | Neethling et al. |
| 2007/0269478 | A1 | 11/2007 | Piconi et al. |
| 2008/0302372 | A1* | 12/2008 | Davidson et al. ............. 128/898 |
| 2009/0164005 | A1 | 6/2009 | Dove et al. |
| 2011/0306123 | A1 | 12/2011 | Strasly et al. |
| 2011/0306124 | A1 | 12/2011 | Strasly et al. |

FOREIGN PATENT DOCUMENTS

EP 0795337 A2 9/1997

OTHER PUBLICATIONS

Pathak et al., J. Biomed. Mater. Res., 69A: 140-144, 2004.*
Stacchino et al., J. of Heart Valve Disease, 7: 190-194, 1998.*
Biological buffers, AppliChem, 2008, pp. 1-20.
European Search Report and Opinion issued in EP Application No. 11167681, dated Oct. 28, 2011, 5 pages.
European Search Report and Opinion issued in EP Application No. 11167695, dated Nov. 7, 2011, 6 pages.
Italian Search Report and Written Opinion issued in IT Application No. TO2010A000486, completed Jan. 17, 2011, 7 pages.
Italian Search Report and Written Opinion issued in IT Application No. TO2010A000487, Jan. 21, 2011, 9 pages.
Pettenazzo, Elena et al., "Octanediol treatement of glutaraldehyde fixed bovine pericardium: evidence of anticalcification efficacy in the subcutaneous rat model", European Jouran of Cardio-thoracic Surgery 34 (2008) 418-422.

* cited by examiner

Primary Examiner — Thaian N Ton
(74) Attorney, Agent, or Firm — Faegre Baker Daniels LLP

(57) ABSTRACT

A method of treating a biological tissue for biological prostheses includes steps of fixation of the biological tissue via a fixing solution including glutaraldehyde and detoxification of the fixed biological tissue via treatment with a detoxifying solution. The detoxification step includes one or both of eliminating phospholipids via treatment with an elimination solution and a treatment with a detoxifying solution. The elimination solution includes 1,2-octanediol and ethanol. The detoxifying solution includes taurine or homocysteic acid.

12 Claims, 3 Drawing Sheets

METHOD FOR PREPARING BIOLOGICAL TISSUES FOR USE IN BIOLOGICAL PROSTHESES

RELATED APPLICATION

This application claims priority to Italian Patent Application No. IT TO2010A000487 filed Jun. 9, 2010, and claims priority to European Application No. 11167695, filed May 26, 2011, both applications are incorporated by reference herein in their entirety.

TECHNICAL FIELD

The present invention is generally directed to a method for detoxifying biological tissue for use in biological prostheses such as prosthetic valves and more particularly to a method for detoxifying biological tissue for use in prosthetic cardiac valves.

BACKGROUND

Biological prostheses are medical devices that utilize animal tissues. Examples of suitable animal tissues include, for example, bovine, porcine, ovine and equine. Depending on the various medical uses, the biological tissue includes cardiac valves, pericardium, tendons, ligaments, dura mater, skin, veins, etc.

The tissues used in biological prostheses are formed primarily of collagen, a protein with a structural unit represented by three polypeptide chains that associate to form a triple helix. The collagen molecules assemble to form microfibrils that in turn assemble to form fibrils that, arranged in corrugated or parallel bundles, give rise to true collagen fibers. Such tissues have good resistance to traction and are flexible but substantially inextensible.

Animal tissues used in biological prostheses are first subjected to numerous washings to eliminate traces of blood and a careful removal of fat and ligaments. However, cells or cellular residues from the animal donor can remain trapped in the structure of the tissue itself. As a result it is possible that the immune system of the host gives rise to a rejection phenomenon that can lead to the destruction of the tissue constituting the biological prosthesis.

An additional problem is degradation of the collagenous biological tissue once implanted in the host organism. For this reason, the biological tissues are subjected to a fixation treatment that has the aim of protecting the tissue for such degradation phenomena and contributing to preventing the above-mentioned rejection phenomenon.

Among the substances used for the fixation of biological tissues, the most common is glutaraldehyde. This bifunctional molecule, carrying two aldehyde groups, is capable of stably binding together free amino groups of the amino acids that constitute the polypeptide chains both within one collagen molecule and between adjacent collagen molecules. In this way glutaraldehyde forms intra-chain and inter-chain bridge structures, causing the cross linking of the biological tissue. Such cross linking protects the tissue from degradation by the host and confers favorable mechanical properties such as for example a better resistance to traction with respect to untreated tissue.

Glutaraldehyde is a highly bactericidal and virucidal substance; therefore, in addition to cross linking the tissue, the fixation step also determines at least a partial sterilization.

In addition, glutaraldehyde is capable of binding to the free amino residues of the membrane proteins of the cellular components still present, masking their antigenic potential and impeding immune activation phenomena and rejection by the host.

In spite of widespread use, glutaraldehyde has a disadvantage of being one of the factors that favor pathological calcification of implanted tissues. The calcium, present in the bodily fluids of the host organism, accumulates on proteinaceous tissue giving rise to a process of, for example in the case of biological cardiac valves, one of the principle cause of valve failure. The calcium deposits can cause reduced flexibility of the portion of biological tissue constituting the valve (or the so-called valve leaflets or cusps) and lead to laceration of the tissue itself, causing a partial or total loss of valve function. The mechanism responsible for the calcification is not yet completely known and is attributed to numerous factors but is know that, following the process of glutaraldehyde fixation, free aldehyde groups that remain on the tissue can create binding sites for calcium.

In addition, phospholipids within the cellular membranes of the cells or cellular residues from the donor animal that remain trapped in the tissue structure also constitute sites for the binding and accumulation of calcium.

To limit the process of calcification in tissues destined for use in biological prostheses, recourse has been taken to various treatments to neutralize the aldehyde residues remaining free after the fixation step and to remove membrane phospholipids. For example, US-A-2006/0193885 describes the use of two solutions, the first containing lower alcohols to remove membrane phospholipids and the second containing arginine, histidine, lysine or salts of aspartic or glutamic acid to neutralize the aldehyde groups present on the biological tissue after fixation. U.S. Pat. No. 6,479,079 describes treatment of biological tissue for the removal of membrane phospholipids with solutions including alcohols having from 4 to 36 carbon atoms. U.S. Pat. No. 5,873,812 describes the use of amino carboxylic acids, for example homocysteic acid, to neutralize the aldehyde residues that remain free on biological tissue after the fixation process.

However, such methods are not ideal solutions because binding sites for calcium remain on the biological tissue, in particular, the neutralization of free aldehyde groups present after the process of fixation with glutaraldehyde is often partial.

SUMMARY

The present invention is directed to improved, more efficacious solutions that limit the calcification of biological tissues after implantation in the host.

In some embodiments, the present invention is directed to a method for treating a biological tissue for biological prostheses.

In some embodiments, the method includes fixation of the biological tissue via a treatment with a glutaraldehyde solution and detoxifying the fixed biological tissues. Detoxification includes a step of eliminating phospholipids via a treatment with an elimination solution including 1,2-octanediol and ethanol as well as a treatment with a detoxifying solution including taurine or homocysteic acid at a temperature above room temperature.

The results shown below demonstrate that the method for the treatment of a biological tissue clearly has advantages if it includes a step of elimination of membrane phospholipids through treatment with an aqueous solution containing 1,2-octanediol and ethanol.

The same method for treatment of a biological tissue has additional advantages when the detoxification step is performed at a temperature above room temperature.

The best results, that is, the most efficacious reduction of the number of free aldehyde groups present on fixed tissue, are obtained when the method envisions conducting both the phospholipid elimination step and the detoxification step at a temperature above room temperature.

Carrying out the method described herein it is possible to obtain a biological tissue for biological prostheses that is much less susceptible to the calcification process when implanted in a host organism with respect to tissue treated with the method of the known art cited above.

BRIEF DESCRIPTION OF THE FIGURES

The invention will now be described in detail, by way of non-limiting example only, with reference to the annexed drawings, in which.

DETAILED DESCRIPTION

Figure 1A:
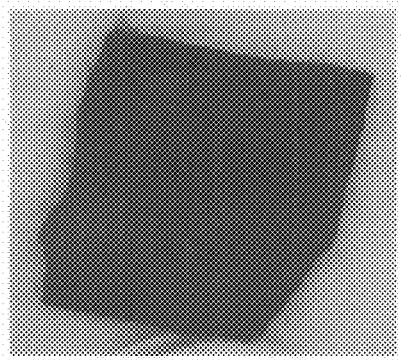
FIG. 1A shows fuchsine staining of a control sample fixed but not detoxified.

The invention will now be described in detail, by way of non-limiting example only, with reference to forming biological prosthetic cardiac valves. It is evident that the method described herein can be used for the preparation of any other biological tissue for forming of other biological prostheses that use, for example tendons, ligaments, dura mater, skin, veins, etc.

In the following description, numerous specific details are given to provide a thorough understanding of the embodiments. The embodiments can be practiced without one or more of the specific details, or with other methods, components, materials, etc. In other instances, well-known structures, materials or operations are not shown or described in detail to avoid obscuring certain aspects of the embodiments.

Reference throughout the present specification to "one embodiment" or "an embodiment" means that a particular feature, structure or characteristic described in connection with the embodiment is included in at least one embodiment. Thus, the phrase "in one embodiment" or "in an embodiment" in various places throughout the present specification are not necessarily all referring to the same embodiment. Furthermore, the details of features, structures, or characteristics may be combined in any suitable manner in one or more embodiments.

The headings provided herein are for convenience only and do not interpret the scope or meaning of the embodiments.

The present description concerns a method for treating a biological tissue that includes the following steps:
i) Fixation of the biological tissue via treatment with a fixing solution containing glutaraldehyde, and
ii) Detoxification of the fixed biological tissue via treatment with a detoxifying solution.

In some embodiments, detoxification of the fixed biological tissue includes a step of membrane phospholipid elimination via treatment with an elimination solution containing 1,2-octanediol and ethanol and—alternatively or in combination—includes treatment with a detoxifying solution containing taurine or homocysteic acid at a temperature above room temperature (20° C.).

In some embodiments, the phospholipid elimination step can be performed on the biological tissue immediately before performing the glutaraldehyde fixation step or before the fixation is completed.

In some embodiments, the phospholipid elimination step can be performed in two distinct stages: a first stage conducted before fixation of the tissue and a second stage conducted simultaneously with the detoxification step, in which the solution containing detoxifying agents (taurine or homocysteic acid) also contains 1,2-octanediol and ethanol.

The aqueous solution containing 1,2-octanediol and ethanol is, in fact, capable of solubilizing the phospholipids of which the membranes of the donor animal cells that remain trapped in the tissue are composed (Pettenazzo et al., 2008, Octanediol treatment of glutaraldehyde fixed bovine pericardium: evidence of anticalcification efficacy in the subcutaneous rat model. Eur J Cardiothorac Surg., 34(2):418-422).

Therefore, such treatment removes both the phospholipids, integral components of cellular membranes, and the cellular debris that forms following the destruction of cells due to solubilization of the phospholipids themselves.

The elimination of membrane phospholipids from the tissue reduces the number of sites available for binding calcium and therefore such treatment represents an additional efficacious approach for limiting the calcification of biological tissue after implantation in the host organism.

The present inventors have also verified that the elimination of phospholipids improves the predisposition of the tissue to fixation with glutaraldehyde. In fact, by eliminating the phospholipids, principle constituents of the membranes of cells that remain trapped in the tissue such as collagen fibers have a more homogeneous spatial distribution that results in improved penetration of glutaraldehyde and therefore in a more efficacious and homogeneous cross linking of the tissue.

In addition, it was discovered by the present inventors that the elimination of phospholipids allows improved penetration of the detoxifying substances (taurine or homocysteic acid) into the fixed biological tissue and consequently a more efficacious neutralization of the unconjugated aldehyde groups present in the tissue following fixation.

In addition, it was verified that conducting the detoxification step at a temperature above room temperature improves the efficacy of the neutralization of the aldehyde groups remaining free after fixation, therefore, very efficaciously reducing the number of sites for binding and accumulation of calcium in biological tissue.

Below, by way of non-limiting example, an embodiment of the method for treatment of a biological tissue object of the present description will be described.

The biological tissues destined for biological prosthetic cardiac valves, that is, bovine, equine or possibly pericardium of other animal species or porcine valve, are harvested from authorized abattoirs.

The tissues are washed and initially prefixed—by means of immersion—for 3 to 13 hours at room temperature in a solution of glutaraldehyde at a concentration expressed as v/v that is in the range of 0.05% to 0.3% in phosphate buffer at pH 7.4. In some embodiments, the solution has a glutaraldehyde concentration expressed as v/v of 0.20%.

In some embodiments, after the prefixation step the tissues are immersed in a treatment solution containing 1,2-octanediol and ethanol for eliminating phospholipids.

The solution containing 1,2-octanediol and ethanol has a 1,2-octanediol concentration v/v that is in the range of 1% to 25%. In some embodiments, the solution has a 1,2-octanediol concentration of 2% to 10%. In some embodiments, the solution has a 1,2-octanediol concentration of 5%. In some embodiments, the solution has an ethanol concentration v/v that is in the range of 25% to 49%. In some embodiments, the solution has an ethanol concentration of 30% to 45%. In some embodiments, the solution has an ethanol concentration of 40%. 1,2-octanediol and ethanol are diluted in physiological solution or in an aqueous solution containing a buffer such as phosphate, citrate, acetate, HEPES (4-(2-hydroxyethyl)-1-piperazine ethane sulfonic acid). The pH of the solution is in the range of 4 to 9. In some embodiments, the pH of the solution is 5 to 8. In some embodiments, the pH of the solution is 7.2.

In some embodiments, the phospholipid elimination step is conducted at a temperature that is in the range of 15° C. to 65° C. In some embodiments, the phospholipid elimination step is conducted at a temperature of 30° C. to 40° C. In some embodiments, the phospholipid elimination step is conducted at a temperature of 37° C. The period of treatment of the tissue with the solution containing 1,2-octanediol and ethanol may vary in the range from 2 hours to seven days. In some embodiments, the treatment period is between 16 to 72 hours.

At the end of the phospholipid elimination step, the tissues are washed repeatedly to eliminate both the residue of the solution containing 1,2-octanediol and ethanol and the solubilized phospholipids and the cellular debris formed.

Next is the step of cutting and shaping—according to known art techniques—to form, for example, cardiac valves. This tissue shaping step is irrelevant to the aims of the method object of the present description.

Successively, the biological tissue is subjected to a process of fixation via immersion of the tissue in a solution containing glutaraldehyde at a concentration expressed as v/v that is in the range of 0.10% to 2.00%. In some embodiments, the solution includes glutaraldehyde at a concentration of 0.30% to 1.00%. In some embodiments, the solution includes glutaraldehyde at a concentration of 0.5%.

In some embodiments, the solution containing glutaraldehyde includes an aqueous solution containing a buffer selected from phosphate, citrate, acetate, HEPES, or borate. In some embodiments, the solution includes a phosphate buffer. The pH of the glutaraldehyde-based solution is in the range of 5 to 8. In some embodiments, the pH is 7.4.

In some embodiments, the fixing method is conducted at a temperature in the range of 4° C. to 30° C. In some embodiments, the fixing method occurs at room temperature (20° C.). The period of exposure of the tissue to the solution containing glutaraldehyde can vary in the range 1 to 20 days. In some embodiments, the exposure period is 3 to 13 days.

After the fixation step, the tissue is washed to remove residual glutaraldehyde not conjugated to the tissue.

Then the tissue is detoxified by means of immersion in a solution containing taurine or homocysteic acid.

In some embodiments, the detoxifying solution includes:
i) taurine at a concentration expressed as w/v in the range 0.10% to saturation of the solution. In some embodiments, the taurine is present at a concentration of 0.7%, or
ii) homocysteic acid at a concentration expressed as w/v in the range from 0.10% to saturation of the solution. In some embodiments, the homocysteic acid is present at a concentration of 0.5% to 5%. In some embodiments, the homocysteic acid is present at a concentration of 1%.

The solution containing the detoxifying substance is prepared in a buffer selected from phosphate, citrate, acetate, HEPES, or borate. In some embodiments, the detoxifying solution is prepared in a phosphate buffer. The pH of such solution is in the range of 4 to 9. In some embodiments, the pH of the solution is in the range of to 8. In some embodiments, the pH of the solution is 7.

The detoxification step is conducted at a temperature above 30° C. In some embodiments, the detoxification step is conducted at a temperature in the range of 35° C. to 45° C. In some embodiments, the detoxification step is conducted at a temperature of 40° C. The period of treatment of the tissue with the detoxifying solution may vary in the range of 2 to 96 hours. In some embodiments, the treatment period is in the range of 12 to 48 hours. In some embodiments, the treatment period is 24 hours.

At the end of the detoxification step, the tissue is subjected to washing.

Finally the detoxified tissue is transferred to a conservation solution without aldehydes in phosphate buffer pH 7 containing preservatives such as parabens.

The results of the present description show that the membrane phospholipid elimination step, in addition to reducing the number of calcium binding sites, leads to a considerable enhancement of the detoxification step, that is, a more efficacious neutralization of the non-conjugated aldehyde groups by the detoxifying substance.

In addition, removal of membrane phospholipids and consequently of the cells trapped in the tissue facilitates more homogeneous cross linking of collagen by glutaraldehyde because of improved penetration of glutaraldehyde into the tissue and improved spatial organisation of the collagen fibers.

At the end of the process, this results in more successful detoxification reactions. The homocysteic acid or taurine penetrate more freely into the tissue and are able to detoxify the tissue to a higher degree.

Pretreatment with a solution of ethanol and octanediol constitutes not only a removal of phospholipids from the tissue, but a preparation of the tissue for a more efficacious cross linking and successive detoxification, acting in synergy with the detoxifying agent.

In addition, carrying out the detoxifying treatment with taurine or homocysteic acid at a temperature above room temperature (approximately equal to 20° C.) leads to greater treatment efficacy, substantially reducing the number of non-conjugated aldehyde groups present in the fixed tissue with respect to a tissue subjected to the same treatment at room temperature.

Now a particular embodiment of the method described herein will be described in detail.

Materials and Methods

Harvesting and Prefixing of Biological Tissue

Biological tissue, including pieces of bovine pericardium harvested from authorized abattoirs, were placed in a physiological solution maintained on ice and transported to the laboratory.

The pieces of pericardium were selected on the basis of thickness and the absence of evident defects, such as dishomogeneity or thickness, the presence of vascularization, cuts, abrasions, etc.

The tissues are prefixed in a solution of glutaraldehyde at 0.20% v/v in phosphate buffer pH 7.4, for a period of time in the range of 3 to 13 hours at room temperature.

Treatment of Tissue for Elimination of Phospholipids

After prefixation, the tissues were immersed in a solution including 5% v/v 1,2-octanediol and 40% v/v ethanol in HEPES buffer at pH 7.2. The treatment had a duration of 16 to 72 hours at 37° C., with gentle agitation. About 200 ml of treatment solution were used for each piece of tissue with dimensions around 10×5 cm.

At the end of the treatment the tissues were washed for 96 hours in saline solution or HEPES pH 7.2 or phosphate buffer pH 7.4. The washing was carried out at room temperature, with vigorous agitation, changing the buffer every 6 to 12 hours, using 200 ml of wash solution for each piece of tissue, at each change.

Next was the step of cutting and shaping the tissue—according to known art techniques—for example, for cardiac valves.

Tissue Fixation

The tissues were fixed for a period in the range 3 to 13 days at room temperature, in a solution of glutaraldehyde 0.50% v/v in phosphate buffer pH 7.4.

At the end of the fixation, the tissues were subjected to washing for 48 hours in phosphate buffer at pH 7 to 7.4 or in sterile physiological solution. Washing was carried out at room temperature, with mild agitation, changing the buffer about every 12 hours, using 200 ml of wash solution for each tissue, at each change.

Tissue Detoxification

The biological tissue was then subjected to detoxification via immersion in an aqueous solution containing i) taurine at a concentration w/v of about 0.70% in phosphate buffer at pH 7, or ii) homocysteic acid at a concentration w/v of 1.00% in phosphate buffer.

The detoxification step was carried out at a temperature higher than room temperature (20° C.), such as at 40° C. for 24 hours.

About 200 ml of detoxifying solution were used for each sample.

At the end of the detoxification step, the tissue was subjected to washing at room temperature in phosphate buffer pH 7, for about three hours, changing the wash solution three times and using about 300 ml of solution for each tissue, at each change.

Finally, the tissues were transferred to a phosphate buffer solution pH 7 containing preservatives such as parabens.

Semiquantitative Determination of Free Aldehyde Groups

Figure 2A:
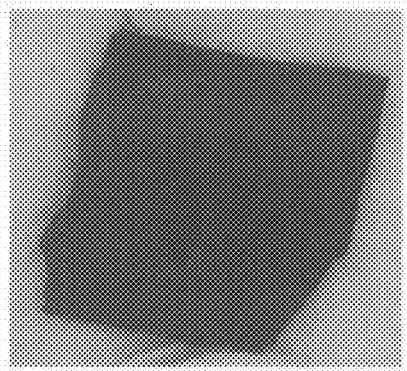
FIG. 2A shows fuchsine staining of a control sample fixed but not detoxified.
Figure 2B:
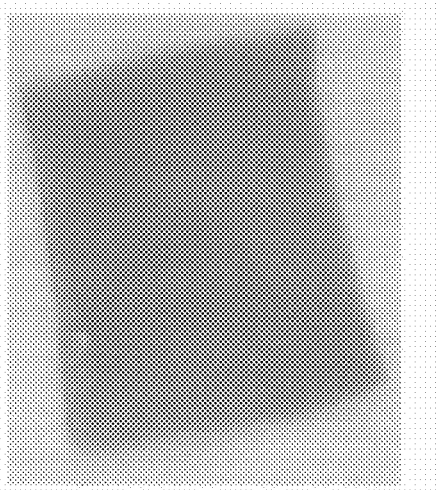
FIG. 2B shows fuchsine staining of a sample that was fixed and detoxified using a homocysteic acid solution at room temperature.
Figure 2D:
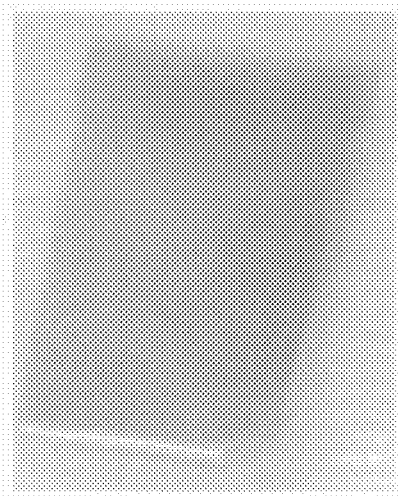
FIG. 2D shows fuchsine staining of a sample that was fixed and detoxified with a solution containing homocysteic acid at 40° C.
Figure 2C:
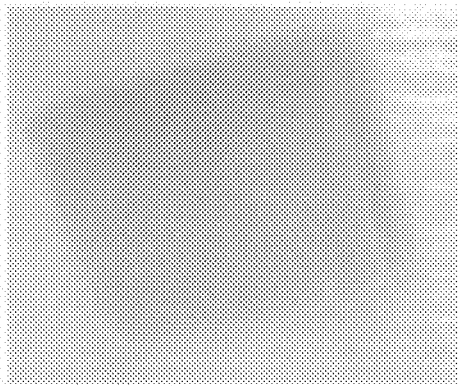
FIG. 2C shows fuchsine staining of a sample that was subjected to removal of phospholipids, fixed and detoxified with a solution containing taurine at room temperature.
Figure 2E:
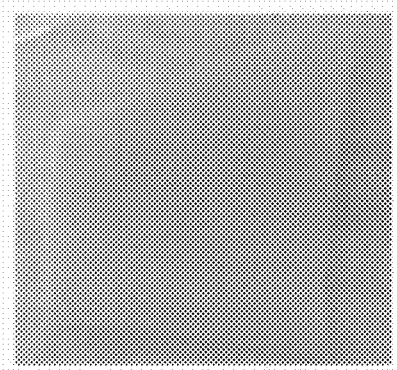
FIG. 2E shows fuchsine staining of a sample that was subjected to removal of phospholipids, fixed and detoxified with a solution containing homocysteic acid at 40° C.

Evaluation of free aldehyde groups, and therefore of the efficacy of the treatment described herein was conducted on two groups of samples, according to what is described in points a) and b) below.

a) To demonstrate the greater efficacy of detoxifying treatment at a temperature higher than room temperature, the present inventors have semiquantitatively determined the number of free aldehyde groups in five biological tissue samples treated as follows:

a first control sample (FIG. 1A) including biological tissue fixed with glutaraldehyde but not detoxified;

a second control sample (FIG. 1B) fixed with glutaraldehyde and detoxified with a solution containing homocysteic acid at room temperature (20° C.);

a third sample (FIG. 1C) fixed with glutaraldehyde and detoxified with a solution containing homocysteic acid at 40° C.

b) To demonstrate that the efficacy of detoxification at a temperature higher than room temperature is enhanced by previous treatment to eliminate membrane phospholipids, the present inventors have semiquantitatively determined the number of free aldehyde groups in another group of biological tissue samples treated as follows:

a first control sample fixed and not detoxified (FIG. 2A);

a second sample fixed and detoxified with a solution containing homocysteic acid at room temperature, 20° C. (FIG. 2B);

a third sample subjected to a treatment for elimination of phospholipids, fixed, and detoxified with a solution containing homocysteic acid at room temperature, 20° C. (FIG. 2C).

a fourth sample fixed and detoxified with a solution containing homocysteic acid at 40° C. (FIG. 2D);

a fifth sample subjected to a treatment for elimination of phospholipids, fixed, and detoxified with a solution containing homocysteic acid at 40° C. (FIG. 2E).

Fuchsine Staining of Tissue

The tissue staining, to detect free aldehyde groups, employs an acidic solution of rosaniline hydrochloride (fuchsine). The staining takes advantage of the formation of bonds between the $NH_2$ groups of the dye and free aldehyde groups on the tissue.

The treatment solution is colorless at first but develops a violet color in the presence of free aldehyde groups on the tissue.

The samples to stain were cut to obtain cards with dimensions of about 1.5×1.5 cm and then immersed in the stain, about 10 ml, each card in a separate test tube.

The stain was 1.00% rosaniline hydrochloride, 4.00% sodium metabisulfite in 0.25 M hydrochloric acid. The tissues remained immersed in the stain for 5 minutes at room temperature, with gentle agitation.

Each card was then transferred to a solution obtained mixing 8 gr of $Na_2SO_3$ and 30 ml of 37% hydrochloric acid, brought to one liter with demineralized water. The cards remain immersed in this wash solution for 10 minutes, with mild agitation.

Next were 2 successive washes for 10 minutes, with mild agitation in wash solution of acidic ethanol, composed of 700 ml of ethanol and 30 ml of 37% hydrochloric acid, brought to one liter with demineralized water.

The washes removed the dye bound non-specifically to the tissue. About 20 ml of wash solution were used at each change.

At the end, the cards were transferred to phosphate buffer pH 7 and photographed, to document differences in staining.

Reflectance Spectroscopy

The stained samples were subjected to reflectance spectroscopy to semiquantitatively evaluate the different chromatic characteristics of the staining with fuchsine.

Reflectance spectroscopy is a technique for optical investigation based on measurement of the spectral reflectance factor of the surface of a sample as a function of the wavelength of the incident radiation. The reflectance parameter is expressed as the ratio of the intensity of the reflected radiation and the incident radiation, as a function of wavelength.

Reflectance measurements were carried out at a wavelength of 570 nm using a Perkin Elmer Lambda 35 spectrophotometer with a spherical integrator. On a scale of values, a lower reflectance value indicates a more intense sample staining and on the contrary a higher reflectance value indicates a weak staining intensity.

Determination of Tissue Phospholipid Content

The present inventors have measured the phospholipid concentration in the biological tissues by means of a spectrophotometric method to demonstrate:

the efficacy of treating tissue with a solution containing 1,2-octanediol and ethanol and that the fixation step and detoxification conducted successive to treatment of the tissue with a solution containing 1,2-octanediol and ethanol do not interfere on the phospholipid content of the tissue.

For this purpose, the quantitative analysis was conducted on samples treated as follows:

a first control sample fixed and not detoxified (FIG. 3A);

a second sample fixed and detoxified with a solution containing homocysteic acid at 40° C. (FIG. 3B);

a third sample subjected to treatment to eliminate phospholipids, fixed and detoxified with a solution containing homocysteic acid at 40° C. (FIG. 3C).

For the spectrophotometric determination of phospholipid content, a 300 mg card was recovered from each treated tissue. Each card is subjected to numerous washings in saline solution without phosphate ions, to remove all residual phosphate buffer. The cards were then removed from the saline solution and blotted to eliminate excess saline solution. The cards were then weighed and triturated. Each card pulverized in this way was extracted in a hot solution of ethanol/ethyl ether 3/1. The extract was then dried.

The extracts were subjected to an acid digestion treatment performed by adding 650 ul of 60% perchloric acid to each sample for 30 minutes at 160° C. This step transformed the phosphorus present into inorganic phosphate which was determined spectrophotometrically. At the end of the 30 minutes the samples were allowed to cool and mixed with a solution constituted of 3.3 ml of distilled water, 500 ul of a solution containing 10% ascorbic acid in distilled water and 500 ul of 1% ammonium molybdate in distilled water. The samples were brought to 100° C. for 5 minutes and centrifuged. Next, the absorbance of the supernatants was read at 820 nm. The phosphate concentration was derived from a standard curve constructed using a solution of known inorganic phosphate concentration as a standard. The phosphate determined in the extracts was proportional to the phospholipid concentration of the samples.

Determination of the Contraction Temperature

The contraction temperature is an index of the level of cross linking of fixed tissue and is determined on pericardial disks of about 5 mm diameter, using a differential scanning calorimeter (DSC) Q100 TA Instruments with the following parameters:

nitrogen flow of 50 ml/min,
heating ramp of 5° C./min,
temperature range 65° C. to 95° C.

Results

Detoxification

The efficacy of the method described herein, and therefore the reaction that takes place between the amino groups of the detoxifying molecule and the aldehyde groups on the fixed tissue, is demonstrated by fuchsine staining of the aldehyde groups remaining free; more intense staining indicates numerous free aldehyde groups and, on the contrary, weaker or absent staining indicates few or no free aldehyde groups on the detoxified tissue.

As demonstrated by the variation in staining intensity of the tissues shown in FIG. 1, increasing the temperature increases the efficacy of the detoxifying treatment. A sample detoxified at 40° C. with taurine, sample E, has a much weaker staining with respect to a control sample, sample A, and with respect to a sample detoxified with taurine at room temperature, sample C.

In the same way, the detoxifying treatment carried out with homocysteic acid at 40° C. results in a weak staining intensity, sample D, with respect to control, sample A, and with respect to the sample treated with homocysteic acid at room temperature, sample B.

Therefore, these results demonstrate higher efficacy of the detoxifying treatment conducted at a temperature higher than room temperature, such as higher than 30° C., using either taurine or homocysteic acid.

These observation are confirmed by the reflectance spectroscopic analysis of the samples. The reflectance of each sample depends on the staining intensity and it is possible to associate a percent reflectance value to each sample by means of reflectance spectroscopic analysis.

A higher reflectance value is associated with weaker staining intensity and vice versa a lower reflectance value is associated with higher staining intensity.

Figure 1B:
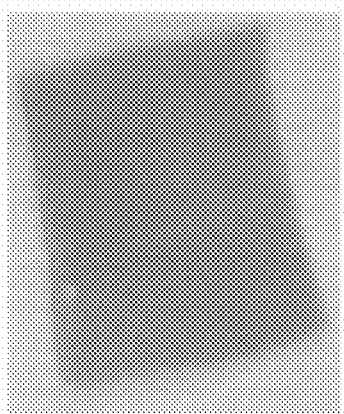
FIG. 1B shows fuchsine staining of a sample that was fixed and detoxified according to the known art using a homocysteic acid solution at room temperature.
Figure 1D:
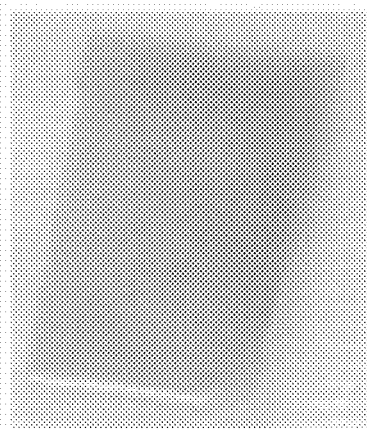
FIG. 1D shows fuchsine staining of a sample that was fixed and detoxified with a homocysteic acid solution at 40 degrees Celsius.
Figure 1C:
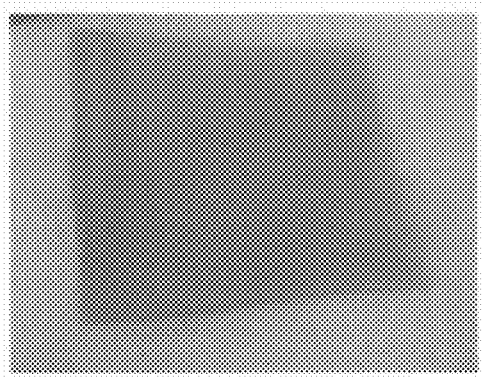
FIG. 1C shows fuchsine staining of a sample that was fixed and detoxified with a taurine solution at room temperature.
Figure 1E:
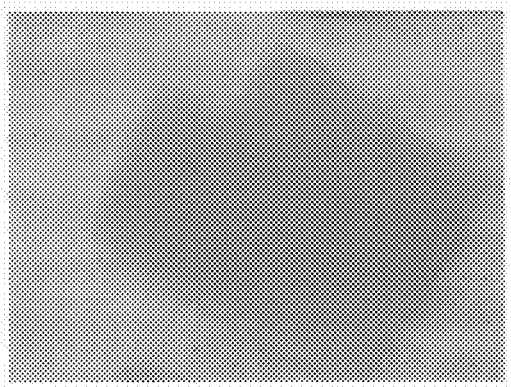
FIG. 1E shows fuchsine staining of a sample that was fixed and detoxified with a taurine solution at 40 degrees Celsius.

As can be seen from the results presented in table 1, the reflectance, analyzed at a wavelength of 570 nm and expressed as a percentage, shows a value of 5.8 for the non-detoxified sample shown in FIG. 1A and higher values, 9 and 13, for samples detoxified with homocysteic acid and taurine, respectively, at room temperature, shown in FIGS. 1B and 1C. Decidedly higher values are observed for samples detoxified with solutions containing homocysteic acid or taurine at 40° C., samples shown in FIGS. 1D and 1E.

TABLE 1

| Sample | Staining observed | Reflectance % at 570 nm |
|---|---|---|
| A-fixed, not detoxified | Very intense purple | 5.8 |
| B-fixed, homocysteic acid room temperature | Violet | 9 |
| C-fixed, taurine room temperature | pale Violet | 13 |
| D-fixed, homocysteic acid 40° C. | Dark pink | 15 |
| E-fixed, taurine 40° C. | pink | 19 |

These results confirm that treatment with taurine or homocysteic acid at 40° C. is more efficacious than the respective treatments conducted at room temperature for neutralization of free aldehyde groups present on fixed tissue.

It was also demonstrated that the phospholipid elimination step that precedes the tissue fixation and detoxification steps enhances the efficacy of taurine or homocysteic acid in neutralizing aldehyde groups remaining free in fixed tissue when the detoxification is conducted at room temperature. FIG. 2 shows that the intensity of staining of samples detoxified with homocysteic acid at room temperature, sample C, after treatment with 1,2-octanediol and ethanol is decidedly lower than the intensity of staining of the sample detoxified with homocysteic acid at room temperature, sample B, without the previous treatment with the solution containing 1,2-octanediol and ethanol to eliminate phospholipids.

Even better results are obtained when the phospholipid elimination step precedes the detoxification step conducted at 40° C. Sample E, subjected to phospholipid extraction treatment and detoxified with homocysteic acid at 40° C. shows a better result with respect to sample D detoxified with homocysteic acid at 40° C. but not subjected to the treatment with 1,2-octanediol and ethanol.

The staining intensity of such samples is decidedly less intense than the staining intensity of non-detoxified control samples, sample A.

The results of reflectance spectroscopic analysis for the samples shown in FIG. 2 are shown in table 2.

TABLE 2

| Sample | Staining observed | Reflectance % at 570 nm |
|---|---|---|
| A-fixed, not detoxified | Very intense purple | 5.8 |
| B-fixed, homocysteic acid room temperature | Violet | 9 |
| C-elimination phospholipids, fixed, homocysteic acid room temperature | Light Violet | 14 |
| D-fixed, homocysteic acid at 40° C. | Dark pink | 16 |
| E-elimination phospholipids, fixed, homocysteic acid at 40° C. | Pale pink/ colourless | 22 |

Even better results are obtained when the detoxification step is conducted with taurine, this being more efficacious than homocysteic acid for neutralizing free aldehyde groups already at room temperature, even without the phospholipid elimination step, as is shown in FIG. 1.

Phospholipid Content

Figure 3:
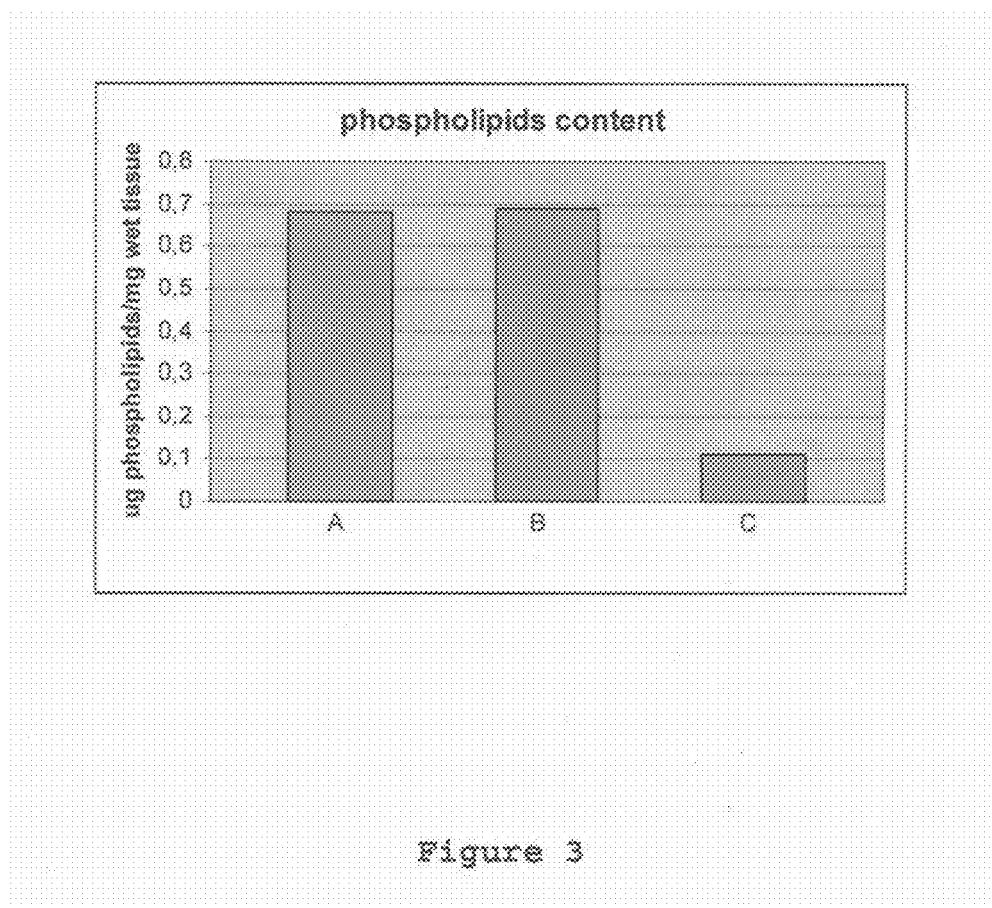
FIG. 3A shows fuchsine staining of a control sample fixed but not detoxified.
FIG. 3B shows fuchsine staining of a sample that was fixed and detoxified with a solution containing homocysteic acid at 40° C.
FIG. 3C shows fuchsine staining of a sample that was subjected to the phospholipid eliminating treatment, fixed and detoxified with a solution containing homocysteic acid at 40° C.

The histogram in FIG. 3 shows that the phospholipid content is significantly lower in tissue samples that were immersed in a solution containing 1,2-octanediol and ethanol, sample C, with respect to a control sample not treated with the same solution, sample A. In addition, it can be seen that the phospholipid content is not influenced by the detoxification step with homocysteic acid at 40° C. alone, sample B.

Contraction Temperature

To verify that the treatment for eliminating phospholipids and the detoxifying treatment do not alter the cross linking of biological tissues obtained by means of their treatment with a solution containing glutaraldehyde, the contraction temperatures for treated tissues are compared with the contraction temperatures of a control tissue fixed and not treated.

The contraction temperatures of tissues fixed and treated with taurine or homocysteic acid, both at room temperature and at higher temperatures, are indistinguishable from the contraction temperature of tissue fixed and not detoxified, that temperature being 85-86° C.

Therefore, the detoxifying treatments do not have significant effects on the level of tissue cross linking.

Actually, when the tissues are subjected to the phospholipid elimination step, fixed and then treated with solutions containing taurine or homocysteic acid a small increase in the contraction temperature is observed. Therefore, this result demonstrates that the tissue subjected to the phospholipid elimination step, fixed and then detoxified has better cross linking.

Without prejudice to the underlying principle of the invention, the details and the embodiments may vary, even appreciably, with reference to what has been described by way of example only, without departing from the scope of the invention as defined by the annexed claims.

We claim:

1. A method of treating a biological tissue for use in a biological prosthesis, the method comprising the steps:
    eliminating phospholipids from the biological tissue via treatment with an elimination solution including 5% v/v 1,2-octanediol and 40% v/v ethanol at a pH of 7.2 and a temperature of 37° C.;
    fixing the biological tissue via a treatment with a fixing solution containing 0.5% v/v glutaraldehyde in phosphate buffer at a pH of 7.4; and
    detoxifying the fixed biological tissue via treatment with a detoxifying solution including taurine or homocysteic acid in phosphate buffer at pH 7 and at a temperature above room temperature.

2. The method according to claim 1, wherein detoxification occurs at a temperature above 30° C.

3. The method according to claim 1, wherein elimination of phospholipids is carried out for a time period in the range of 2 to 7 days.

4. The method according to claim 1, wherein elimination of phospholipids is carried out for a time period in the range of 16 to 72 hours.

5. The method according to claim 1, wherein the detoxifying solution includes taurine at a concentration expressed as w/v in the range from 0.10% to saturation.

6. The method according to claim 1, wherein the detoxifying solution includes taurine at a concentration expressed as w/v in the range of 0.20% to 1.00%.

7. The method according to claim 1, wherein the detoxifying solution includes homocysteic acid at a concentration expressed as w/v in the range from 0.10% to saturation.

8. The method according to claim 1, wherein the detoxifying solution includes homocysteic acid at a concentration expressed as w/v in the range of 0.50% to 5.00%.

9. The method according to claim 1, wherein the detoxification step is carried out at a temperature greater than 30° C.

10. The method according to claim 1, wherein the detoxification step is carried out at a temperature between 35° C. and 45° C.

11. The method according to claim 1, wherein the detoxification step is carried out for a period in the range of 2 to 36 hours.

12. The method according to claim 1, wherein the detoxification step is carried out for a period of 12 to 48 hours.

* * * * *